(12) United States Patent
Wilsey

(10) Patent No.: US 11,806,069 B2
(45) Date of Patent: Nov. 7, 2023

(54) DEVICES AND METHODS FOR THE DIAGNOSIS AND TREATMENT OF DISCOGENIC BACK PAIN

(71) Applicant: Warsaw Orthopedic, Inc., Warsaw, IN (US)

(72) Inventor: Jared Wilsey, Memphis, TN (US)

(73) Assignee: Warsaw Orthopedics, IN, Warsaw, IN (US)

( * ) Notice: Subject to any disclaimer, the term of this patent is extended or adjusted under 35 U.S.C. 154(b) by 882 days.

(21) Appl. No.: 16/257,905

(22) Filed: Jan. 25, 2019

(65) Prior Publication Data
US 2020/0237436 A1 Jul. 30, 2020

(51) Int. Cl.
*A61B 18/14* (2006.01)
*A61B 17/32* (2006.01)
(Continued)

(52) U.S. Cl.
CPC .. *A61B 18/1477* (2013.01); *A61B 17/320068* (2013.01); *A61B 18/20* (2013.01);
(Continued)

(58) Field of Classification Search
CPC ..... A61B 18/1477; A61B 18/14; A61B 18/12; A61B 18/04; A61B 18/042; A61B 18/20;
(Continued)

(56) References Cited

U.S. PATENT DOCUMENTS

| 5,304,141 A | * | 4/1994 | Johnson | A61B 17/3401 604/512 |
| 5,433,739 A | | 7/1995 | Sluijter et al. | |

(Continued)

FOREIGN PATENT DOCUMENTS

| CN | 101041101 A | 9/2007 |
| CN | 101077313 A | 9/2007 |

(Continued)

OTHER PUBLICATIONS

Disease, G.B.D., I. Injury, and C. Prevalence, Global, regional, and national incidence, prevalence, and years lived with disability for 328 diseases and injuries for 195 countries, 1990-2016: a systematic analysis for the Global Burden of Disease Study 2016. Lancet, 2017. 390(10100): p. 1211-1259. Abstract.

(Continued)

*Primary Examiner* — Emily L Schmidt
*Assistant Examiner* — Alexandra Lalonde
(74) *Attorney, Agent, or Firm* — Sorell, Lenna & Schmidt, LLP; William D. Schmidt (57) ABSTRACT

A device is provided for supplying electrical current to an intervertebral disc. The device comprises a cannula having a proximal end and a distal end and a longitudinal axis therebetween. The distal end comprises a beveled tip for contacting a region of the intervertebral disc, and an electrode disposed within or on a surface of the cannula adjacent to the distal end. The electrode is configured to discharge electrical current to the region of the intervertebral disc. Methods of diagnosing and/or treating discogenic back pain are also provided.

10 Claims, 8 Drawing Sheets

(51) Int. Cl.
*A61N 1/05* (2006.01)
*A61B 18/20* (2006.01)
*A61B 18/00* (2006.01)

(52) U.S. Cl.
CPC .... *A61N 1/0551* (2013.01); *A61B 2018/0044* (2013.01); *A61M 2210/1003* (2013.01)

(58) Field of Classification Search
CPC ............ A61B 18/18; A61B 17/320068; A61B 17/22012; A61B 2018/004; A61B 2018/00434; A61B 2018/00315; A61N 1/0551; A61N 1/05; A61N 1/04; A61N 1/02; A61N 1/00; A61N 2/00; A61N 1/36062; A61N 1/36071; A61N 1/3605; A61M 1/84; A61M 1/842; A61M 1/85; A61M 1/86; A61M 5/158; A61M 5/14; A61M 5/28; A61M 5/24; A61M 5/178; A61M 5/32; A61M 5/3286; A61M 25/06; A61M 25/01; A61M 2210/1003

See application file for complete search history.

(56) References Cited

U.S. PATENT DOCUMENTS

| | | |
|---|---|---|
| 6,602,248 B1 | 8/2003 | Sharps et al. |
| 7,634,307 B2 | 12/2009 | Sweeney |
| 8,597,192 B2 | 12/2013 | McKay |
| 9,492,461 B2 | 11/2016 | King et al. |
| 2002/0120259 A1 | 8/2002 | Lettice et al. |
| 2003/0158545 A1 | 8/2003 | Hovda et al. |
| 2004/0024396 A1* | 2/2004 | Eggers ............... A61B 18/1482 606/39 |
| 2005/0240126 A1 | 10/2005 | Foley et al. |
| 2006/0100547 A1 | 5/2006 | Rabiner et al. |
| 2006/0184069 A1 | 8/2006 | Vaitekunas |
| 2006/0224223 A1 | 10/2006 | Podhajsky et al. |
| 2007/0185367 A1 | 8/2007 | Abdou |
| 2007/0255379 A1* | 11/2007 | Williams ................. A61N 1/05 607/116 |
| 2010/0168732 A1 | 7/2010 | Podhajsky et al. |
| 2011/0077628 A1* | 3/2011 | Hoey ..................... A61B 18/04 607/105 |
| 2012/0089123 A1 | 4/2012 | Organ et al. |
| 2016/0095721 A1* | 4/2016 | Schell .................. A61F 2/4611 623/17.16 |
| 2016/0317621 A1 | 11/2016 | Schnitzspan et al. |
| 2017/0049507 A1 | 2/2017 | Cosman et al. |
| 2017/0119432 A1 | 5/2017 | McKay |
| 2018/0036060 A1* | 2/2018 | Wegrzyn, III ....... A61B 18/082 |
| 2018/0272132 A1 | 9/2018 | Subbaroyan et al. |
| 2019/0076168 A1* | 3/2019 | Jameson ............ A61B 17/3468 |

FOREIGN PATENT DOCUMENTS

| | | |
|---|---|---|
| CN | 201431510 Y | 3/2010 |
| CN | 102091382 A | 6/2011 |
| CN | 103751011 A | 4/2014 |
| CN | 104739504 A | 7/2015 |
| CN | 103978276 B | 5/2016 |
| CN | 105534595 A | 5/2016 |
| EP | 1459691 A1 | 9/2004 |
| EP | 2229171 A2 | 9/2010 |
| KR | 101338635 B1 | 12/2013 |

OTHER PUBLICATIONS

Peng, B.G., Pathophysiology, diagnosis, and treatment of discogenic low back pain. World J Orthop, 2013. 4(2): p. 42-52. Abstract.
Jabbari, B. and D. Machado, Treatment of refractory pain with botulinum toxins—an evidence-based review. Pain Med, 2011. 12(11): p. 1594-606. Abstract.
Singh, J.A., M.L. Mahowald, and S. Noorbaloochi, Intraarticular botulinum toxin A for refractory painful total knee arthroplasty: a randomized controlled trial. J Rheumatol, 2010. 37(11): p. 2377-86. Abstract.
Marchini, C., et al., Efficacy of botulinum toxin type A treatment of functional impairment of degenerative hip joint Preliminary results. J Rehabil Med, 2010. 42(7): p. 691-3. Abstract.
Hadley, H.S., J.L. Wheeler, and S.W. Petersen, Effects of intra-articular botulinum toxin type A (Botox) in dogs with chronic osteoarthritis. Vet Comp Orthop Traumatol, 2010. 23(4): p. 254-8. Abstract.
Chou, C.L., et al., Therapeutic effects of intra-articular botulinum neurotoxin in advanced knee osteoarthritis. J Chin Med Assoc, 2010. 73(11): p. 573-80. Abstract.
Boon, A.J., et al., Efficacy of intra-articular botulinum toxin type A in painful knee osteoarthritis: a pilot study. PM R, 2010. 2(4): p. 268-76. Abstract.
Anderson, S., et al., Analgesic effects of intra-articular botulinum toxin Type B in a murine model of chronic degenerative knee arthritis pain. J Pain Res, 2010. 3: p. 161-8. Abstract.
Goyal, N., Intra-articular knee joint Botox injection for chronic osteoarthritic pain. Anaesth Intensive Care, 2008. 36(1) p. 123. Abstract.
Bertoni, M., et al., Administration of type A botulinum toxin after total hip replacement. Eur J Phys Rehabil Med, 2008. 44(4): p. 461-5. Abstract.
Namazi, H. and Z. Majd, Botulinum toxin and osteoarthritis: greater expectations. Med Hypotheses, 2007. 68(5): p. 1188. Abstract.
DePuy, T., et al., Effects of intra-articular botulinum toxin type A in an equine model of acute synovitis: a pilot study. Am J Phys Med Rehabil, 2007. 86(10): p. 777-83. Abstract.
Namazi, H., Botulinum toxin as a novel addition to anti-arthritis armamentarium: an experimental study in rabbits. Int Immunopharmacol, 2006. 6(11): p. 1743-7. Abstract.
Mahowald, M.L., J.A. Singh, and D. Dykstra, Long term effects of intra-articular botulinum toxin A for refractory joint pain. Neurotox Res, 2006. 9(2-3): p. 179-88. Abstract.
Supplementary European Search Report dated Sep. 28, 2022 by the European Patent Office in corresponding European patent application No. EP 19911445.5.
China National Intellectual Property Administration. Notice on the First Office Action. dated Apr. 23, 2023. Application No. 201980089828. X, 8 pgs.

* cited by examiner

DEVICES AND METHODS FOR THE DIAGNOSIS AND TREATMENT OF DISCOGENIC BACK PAIN

BACKGROUND

Discogenic back pain is a troublesome disorder of the spinal column, where one or more intervertebral discs are the source of pain. It is estimated that one out of every three patients with chronic low back pain have discogenic back pain and that about five percent of the adult population suffers from this disorder.

The spinal column is made up of a series of interlocking bones called vertebrae that are separated by intervertebral discs. The spine provides load-bearing support for one-half of the body's mass and it protects the nerves of the spinal column. Intervertebral discs contain two parts; an annulus fibrosus which is an outer ring-like structure and a nucleus pulposus which is the gel-like interior of the disc void of nerves. However, the outer third of the annulus fibrosus contains nerve fibers. The intervertebral discs provide shock absorption and facilitate the bending of the spine. The combination of the vertebrae and intervertebral discs at each vertebral segment allows for motion of the spine, in particular, flexing, rotation, and extension. The motion and support functions of the spine, in combination with the many interlocking parts and nerves associated with the spinal column, can result in back pain, such as discogenic back pain due to various reasons.

Discogenic back pain can include bulging, herniated, or ruptured discs which can trigger a response from adjacent nerves, causing the pain sensation. Even after a herniated disc heals, the anatomy of the disc may not return to normal and may continue to cause pain. Even in the case where a disc is not herniated, chronic pain may present itself as people age because the annulus fibrosus begins to decay and the resulting small tears in the wall are infiltrated by nerves and blood vessels, causing pressure and chronic pain.

One common way to diagnose a patient with discogenic back pain is through the use of a diagnostic procedure known as discography. During this procedure, selected intervertebral discs are pressurized with an injected sterile liquid to induce pain in the affected intervertebral discs. However, this procedure involves full-thickness penetration of the annulus and injection of contrast media, making the procedure somewhat invasive which can increase the risk of disc degeneration.

Once a disc or discs in pain are diagnosed, the disc or discs can be treated through various surgical or non-surgical methods. However, there is a need for devices and methods that both diagnose and treat discogenic back pain that are less invasive than the standard procedures currently available.

SUMMARY

Devices and methods are provided that allow for a less invasive option in diagnosing and treating discogenic back pain. In various embodiments a device is provided for supplying electrical current to an intervertebral disc. The device comprises a cannula having a proximal end and a distal end and a longitudinal axis therebetween. The distal end comprises a beveled tip for contacting a region of the intervertebral disc, and an electrode disposed within or on a surface of the cannula adjacent to the distal end. The electrode is configured to discharge electrical current to the region of the intervertebral disc.

In some embodiments, a method of diagnosing discogenic back pain is provided. The method comprises administering electrical current from a device to a region of the intervertebral disc, the device comprising a cannula having a proximal end and a distal end and a longitudinal axis therebetween, the distal end comprising a beveled tip for contacting a region of the intervertebral disc, an electrode disposed within or on a surface of the cannula adjacent to the distal end, the electrode configured to discharge electrical current to the region of the intervertebral disc.

In some embodiments, a method of diagnosing and treating discogenic back pain is provided. The method comprises administering electrical current from a device to a region of the intervertebral disc, the device comprising a cannula having a proximal end and a distal end and a longitudinal axis therebetween, the distal end comprising a beveled tip for contacting a region of the intervertebral disc, an electrode disposed within or on a surface of the cannula adjacent to the distal end, the electrode configured to discharge electrical current to the region of the intervertebral disc to evoke a pain response; and administering an effective amount of a neurotoxin to the intervertebral disc to reduce the back pain.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 1 is a perspective view of a device in use for supplying electrical current to an intervertebral disc to diagnose the intervertebral disc for a positive pain response. A beveled tip of the device is directed toward the dorsolateral annulus fibrosus under image guidance. For the diagnostic phase, the tip will not be advanced past the outermost layers of the annulus. The tip of the device allows for separation of the collagenous fibers when rotated parallel to the lamella of the annulus fibrosia. Constant current pulses from about 2 to about 20 mAMP from an electrode attached to the device is delivered to the annulus fibrosus. Concordant pain, and especially pain that is evoked from a low constant pulse or amplitude current, is consistent with nerve ending sensitization and discogenic pain which would be a positive diagnosis. In some embodiments, a syringe can be attached to a port on the device to administer anesthetic and/or neurotoxins to the disc in pain, where the device is a single-lumened needle with an integrated electrode.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Devices and methods are provided that allow for a less invasive option in diagnosing and treating discogenic back pain. The following description is presented to enable any person skilled in the art to make and use the present disclosure. Descriptions of specific embodiments and applications are provided only as examples and various modifications will be readily apparent to those skilled in the art.

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

Definitions

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the device and/or cannula portion of the device that is described herein, and "rearward" or "proximal" (and forms thereof) means rearward or away from the direction of the forward, distal end of the device and/or cannula portion of the device that is described herein. However, it should be understood that these uses of these terms are for purposes of reference and orientation with respect to the description and drawings herein, and are not intended to limit the scope of the claims.

Spatially relative terms such as "under," "below," "lower," "over," "upper," and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc., and are also not intended to be limiting. Like terms refer to like elements throughout the description.

As used herein, the terms "having," "containing," "including," "comprising," and the like are open ended terms that indicate the presence of stated elements or features, but do not preclude additional elements or features.

The term "discogenic back pain" refers to a disorder where one or more intervertebral discs are the source of pain. Discogenic back pain can include bulging, herniated, or ruptured discs which can trigger a response from proximate nerves, causing a pain sensation.

The headings below are not meant to limit the disclosure in any way; embodiments under any one heading may be used in conjunction with embodiments under any other heading.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Device

As shown in FIGS. 1-4, a device 10 is provided for diagnosing and/or treating discogenic back pain. The device is configured to provide electrical current to an intervertebral disc D1 to diagnose a disc that is in pain. The device is also configured for treating discogenic back pain by administering a local anesthetic and a neurotoxin to silence sensitized nerve endings within the disc.

The device comprises a cannula 12 having a proximal end 14, a distal end 16 and a longitudinal axis XX disposed therebetween. The cannula is designed to cause minimal physical trauma to the disc of a patient. The cannula may alternatively be a needle. In some embodiments, a stylet may close the lumen of the needle during placement, running the length of longitudinal axis XX, with removal prior to administering a therapeutic substance.

Figures 2, 2A, 2B:
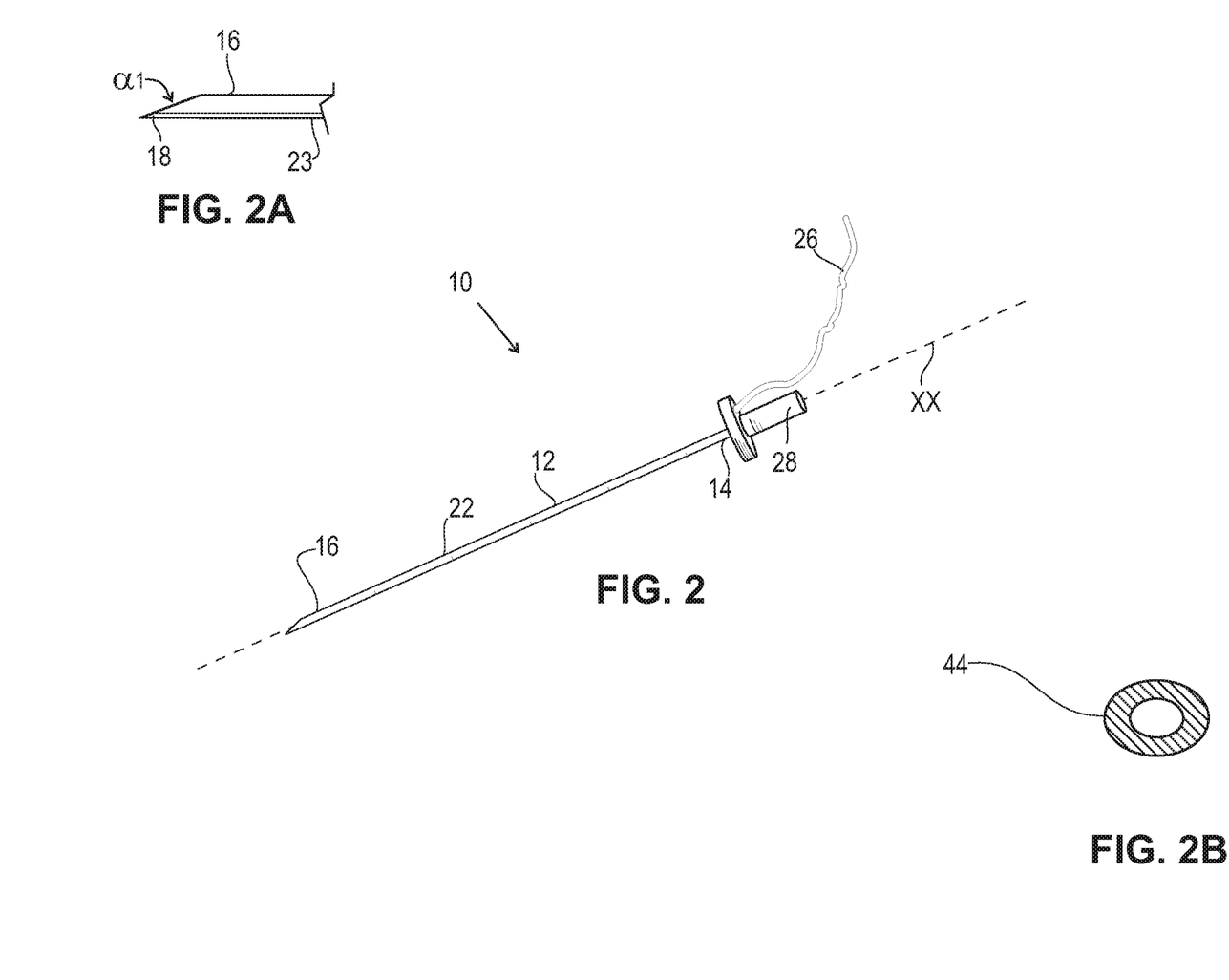
FIG. 2 is a perspective view of the device of FIG. 1 shown with a wire disposed at the proximal end for connecting the electrode to a power source such as an electrical generator.
FIG. 2A is a magnified view of a beveled tip at the distal end of the device of FIG. 2.
FIG. 2B is a cross sectional front view of the cannula and insulation material that is coated or layered within or on the cannula.

The distal end of the cannula comprises a beveled tip 18, as shown in FIG. 2A, configured for contacting a region of the intervertebral disc. The region of the intervertebral disc can be the annulus fibrosus of an intervertebral disc. The beveled tip facilitates separation of the collagenous fibers when rotated parallel to the lamella of the annulus fibrosis. The beveled tip can be sharp and include an angle $\alpha 1$ from about 5 degrees to about 60 degrees. In some embodiments, angle $\alpha 1$ can be from about 5, 10, 15, 20, 25, 30, 35, 40, 45, 50, 55 or 60 degrees. In some embodiments, the beveled tip and/or cannula comprises an air gap 23 disposed in an inner layer of the cannula that functions as insulation to allow controlled delivery of the current to the target tissue site. In some embodiments, an indicator on the proximal end of the device can mark the direction of the bevel.

An electrode 26 is disposed within or on a surface 22 of the cannula adjacent to the distal end. In some embodiments, the electrode can be a wire that runs along the needle or cannula, such that the tip of the electrode is near the top of the needle. It is from the tip that current travels into tissue.

The electrode is configured to discharge electrical current to a region of the intervertebral disc to determine whether a disc is in pain. In some embodiments, a unipolar electrode can be used that has a grounding pad placed on the patient's body. For example, when a disc is the cause of pain in a patient, the electrical current discharged will create a positive pain response in the patient. In some embodiments, more than one electrode can be disposed within or on the surface of the cannula. In some embodiments, 1, 2, 3, 4, 5, 6, 7, 8, 9 or 10 electrodes can be disposed within or on the surface of the cannula. Electrodes may be arranged in a bipolar arrangement, with the distal end of a return electrode approximately 0.1-10 mm proximal to the active electrode.

In some embodiments, the active electrode discharges from about 0.5 to about 50 mAMP pulses of current, or from about 2 to about 20 mAMP pulses of current. In some embodiments, the electrode discharges from about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 mAMP pulses of current.

In some embodiments, the electrical current is administered to a region of the intervertebral disc in pulses. In some embodiments, the electrical current is administered over a period of time, such as, for example, from about 1 to about 10 seconds. In some embodiments, the electrical current is administered over a period of 1, 2, 3, 4, 5, 6, 7, 8, 9 to about 10 seconds.

Figure 4:
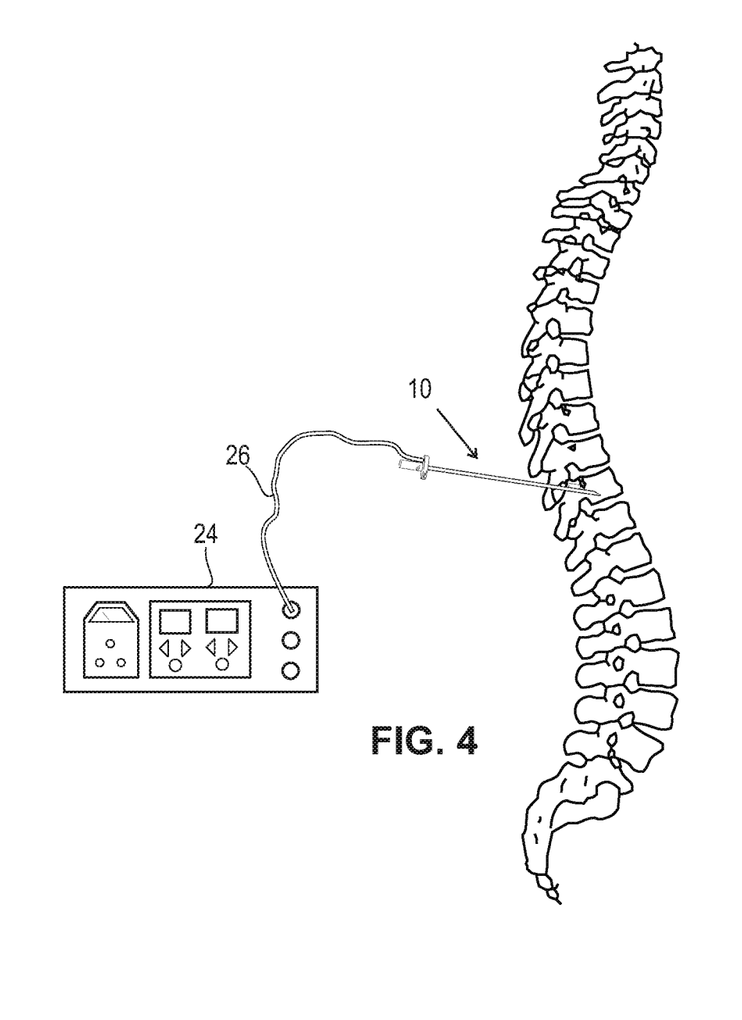
FIG. 4 is a perspective view of the device of FIG. 1 connected to a power source. A spine of a patient is shown and the device is depicted approaching the dorsolateral annulus of the disc.

The proximal end is configured to be coupled to an electrical generator 24 by electrode 26, as shown in FIG. 4. The electrical generator can be an electrical pulse generator.

Figure 3:
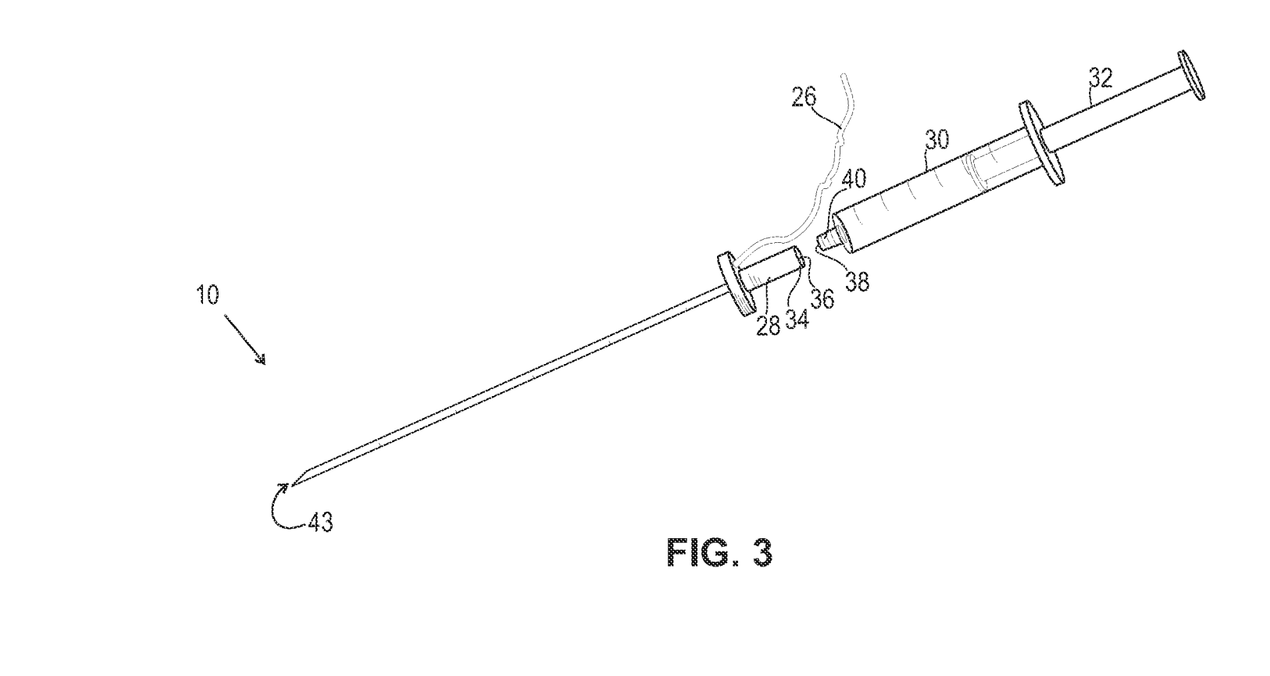
FIG. 3 is a perspective view of the device coupled with a syringe for administering a local anesthetic, anti-inflammatory and/or a neurotoxin through a channel of the cannula to treat an intervertebral disc that tested positive for pain during diagnostics.

In some embodiments, the proximal end of the cannula comprises a port 28 for engagement with a syringe 30 having a plunger 32. The port and syringe engagement facilitates administration of a local anesthetic, anti-inflammatory and/or a neurotoxin through a channel 43 within the cannula to treat an intervertebral disc that tested positive for pain during discharge of an electrical current from the device to the selected intervertebral disc.

The port is in alignment with longitudinal axis XX. Alternatively, in some embodiments, the port can be angled relative to longitudinal axis XX and can be positioned at an angle that is 5 to about 90 degrees relative to longitudinal axis XX. In some embodiments, the angle can be from about 5, 10, 15, 20, 25, 30, 35, 40, 45, 50, 55, 60, 65, 70, 75, 80, 85 to about 90 degrees relative to longitudinal axis XX.

In some embodiments, a proximal end 34 of the port includes an interior surface that defines threading 36 that is configured for engagement with threading 40 on an end 38 of the syringe. In some embodiments, the end of the syringe can be a leer lock fitting.

The syringe is configured for administration of a local anesthetic, an anti-inflammatory and/or a neurotoxin. In some embodiments, the local anesthetic is lidocaine, clonidine, bupivacaine, ropivacaine, mepivacaine, etidocaine, levobupivacaine, trimecaine, carticaine, articaine or a combination thereof. Alternatively, opioid analgesics can be administered such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

In some embodiments, the anti-inflammatory includes, but is not limited to a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents can also include other compounds such as steroids, such as for example, fluocinolone, cortisol, cortisone, hydrocortisone, fludrocortisone, prednisone, prednisolone, methylprednisolone, triamcinolone, betarnethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

In some embodiments, the neurotoxin can include, but is not limited to inhibitors of sodium channels, neurotoxins targeting transient receptor potential cation channel subfamily V member 1 (TRPV1), botulinum toxins or a combination thereof, in particular, inhibitors of sodium channels include, but are not limited to, saxitoxin, μ-conotoxin, tetrodotoxin, batrachotoxin, grayanotoxin, α-scorpion toxins (e.g., bukatoxin), β-scorpion toxins, and brevetoxin. In some embodiments, tarantula toxins with relative selectivity for sodium channels specific to pain fibers may be used for selective silencing of nociception in the disc. In some embodiments, this includes Δ-theraphotoxin-Hm1a and Δ-theraphotoxin-Hm1b.

In some embodiments, the neurotoxins targeting TRPV1 include, but are not limited to, capsaicin and its analogues (homocapsaicin, homodihydrocapsaicin, nonivamide, nordihydrocapsaicin, dihydrocapsaicin), resinferatoxin or a combination thereof.

In some embodiments, alternative strategies for targeting NAV1.7 and/or TRPV1 may include administration of monoclonal antibodies for one or both of these pain fiber cation channels. In some embodiments, botulinum toxins can be administered including, but not limited to both botulinum toxin A and botulinum toxin B. In the case of botulinum toxins, analgesia may be inhibited by a suppression in Nav1.7 channel expression. Inhibition of acetylcholine neurotransmitter release is not relevant to this indication.

In some embodiments, the neurotoxin is administered in an amount of 1 to about 100 μM to the selected area of the disc. In some embodiments, the neurotoxin is administered in an amount of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 μM.

In some embodiments, inhibitors of sodium channels may be administered in a range from about 1 to 100 μM in the maximum recommended injection volume of 500 μL per disc. In some embodiments, when bukatoxin is administered, up to 0.72 mg/mL or up to 0.36 mg delivered in microinjections totaling 500 μL can be administered. In some embodiments, individual microinjections can range from about 10 to about 100 μL as the tip of the device is moved to different regions of the annulus to ensure adequate exposure of all sensitized nerve endings in a disc that tests positive for pain.

In some embodiments, for TRPV1 agonists such as capsaicin, microinjections may contain from 0.1 to 10% of active. In some embodiments, the maximum recommended injection volume is 500 μL (which may be divided into multiple microinjections from 10 to 100 μL) which is equivalent to a dose range of 0.5 to 50 mg.

In some embodiments, for botulinum toxins A and B, a total intra-annular dose of 50 to about 500 IU, or approximately 0.5 to 5.0 ng of protein, can be administered. In some embodiments, administration of the sodium channel inhibitors and TRPV1 agonists will not exceed 500 μL in a total injection volume.

In some embodiments, monoclonal antibodies can be administered in an amount of about 1 to about 100 nM. In some embodiments, to compensate for dilution upon administration of a solution of IgG antibodies to NaV1.7 or TRPV1, the injectate may be at a concentration of 1 to 100 μM. For the typical IgG monoclonal antibody, this will be approximately 150 ng/mL to 15 μg/mL. In some embodiments, the maximum volume administered to the annulus fibrosus is 500 μL per disc, which may be divided into multiple microinjections in different areas of the an fibrosus.

In some embodiments, the large peptide structure of most of the neurotoxins described above are expected to facilitate containment within the targeted disc upon microinjection of solution or small particle suspensions. This, in turn, mitigates the risk of off target effects following migration to adjacent neurological structures or systemic absorption and distribution.

In some embodiments, the neurotoxins or monoclonal antibodies can be delivered in a semi-solid depot form, and the total dose (mg) may be adjusted up to 10 times higher than the doses described above when delivered as a solution.

In some embodiments, the local anesthetic, an anti-inflammatory and/or a neurotoxin is injected in a liquid carrier such as sterile water, bacteriostatic water for injection (BWFI), a pH buffered solution (e.g. phosphate-buffered saline), sterile saline solution, Ringer's solution or dextrose solution.

In some embodiments, the cannula can include an insulation material 44, as shown in FIG. 2B that can be coated or layered within or on the device. In some embodiments, the insulation material is not disposed within or on the beveled tip of the cannula. In some embodiments, the insulation material can be disposed around the electrode. In some embodiments, the insulation material includes, but is not limited to, a silicone elastomer, polyurethane, silicone/polyurethane, glass, porcelain, ceramic, composite polymers, rubber, an air gap, heat resistant plastic or a combination thereof. In some embodiments, the heat resistant plastics include, but are not limited to, PMMA, PET, PEEK, PLA, PLGA, PVC and/or HDPE in some embodiments, rubbers include, but are not limited to silicone, flurosilicone, isobutylene-isoprene copolymer, chlorobutyl, fluroelastomers, and/or polychloroprene.

In some embodiments, the coating or layer of insulation material can have a thickness from about 0.005 to about 4 mm thick. In some embodiments, the thickness can be from about 0.005, 0.01, 0.05, 0.1, 0.2, 0.3, 0.4, 0.5, 0.6, 0.7, 0.8, 0.9, 1, 2, 3 to about 4 mm thick.

In some embodiments, the cannula can be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof.

In some embodiments, the gauge of the cannula is greater than 21 gauge. In some embodiments, the gauge of the cannula can be in the range of 21-34 gauge. In some embodiments, the cannula can be from about 20 to 150 mm in length. In some embodiments, the tip of the cannula can be tapered.

In some embodiments, the cannula or needle can provide a tactile-type tip, which is flattened or blunt to allow the user to better place the tip at or near the desired target tissue site in the spine.

In various embodiments, the cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the cannula relative to the absence of the material or topography.

In some embodiments, a lubricant is provided to assist in the insertion of the tip of the cannula into portions of the annulus fibrosis. In some embodiments, the lubricant can be, without limitation, polyethylene glycol (PEG), hyaluronic acid, hyaluronan, lubricin, polyethylene glycol, and any combinations thereof. In some embodiments, salts may be added to the lubricant to increase conductivity and facilitate passage of electrical current to the annular nerve endings. The salts can include calcium chloride, sodium chloride or a combination thereof.

In various embodiments, the tip is configured to match other anatomical tissue shapes to treat other painful conditions. In certain embodiments, the tip may be introduced at a specific depth to locally provide diagnostics and treatment to a portion of the intervertebral disc site while avoiding damage to other areas that are not intended to be diagnosed or treated.

In some embodiments, the cannula includes indicia, for example a depth indicator that may include an analog, such as, for example, a dial with a numerical indicator of angle and/or digital display, such as, for example, LED and/or LCD. The graduations may represent various indicia, such as, for example, numerical, alphabetic and/or specific conditions/orientations, such as, initial depth and/or final depth of penetration into the annulus fibrosus.

In some embodiments, monitoring devices can be coupled to the device comprising sensors that may receive and record data relating to density, impedance, and position of the tip of the cannula in the form of radiowaves, microwaves, spectroscopy, and the like. In different embodiments, sensors comprising a battery, an electrode, a recharger, a transmitter, a receiver, a transceiver, a sensor, a recorder, a capacitor, a transformer, a system control unit, a programmer, an address/positioning unit, a depth sensor, a pressure sensor, a pressure adjuster, a mechanical power generator, a photo/light generator, an ultraviolet light generator, an infrared generator, an optical stimulator, a laser, a radiofrequency generator, a magnetic field generator, a mechanical vibration generator, an ultrasonic wave generator, an electrical field generator, a radiation generator or a fuel cell can be coupled to the device. In some embodiments, the monitoring device may be a recording electrode placed cranial to the target disc, such as in the epidural space or in or near a dorsal root ganglion.

In various aspects, the device can also be coupled to an imaging modality such as ultrasound, CT, fluoroscopy or MRI, overhead 3D stereotactic system (via pre-procedure MRI and/or CT) allowing the user to visualize or otherwise identify the intervertebral disc. For example, imaging devices useful in coupling with the device described herein comprise, without limitation, Magnetic Resonance Imaging (MRI), functional Magnetic Resonance Imaging (fMRI), Magnetic Resonance Spectroscopy (MRS), diffusion MRI (DWI), diffusion tensor MRI (DTI), electroencephalography (EEG), magnetoencephalography (MEG), nuclear neuroimaging, positron emission tomography (PET), single photon emission computed tomography (SPECT), Ictal-Interictal SPECT Analysis by Statistical Parametric Mapping (ISAS), Computed Tomography (CT), x-ray, fluoroscopy, angiography, ultrasonography, transcranial magnetic stimulation (TMS), transcranial direct current stimulation (tDCS), transcranial electrical stimulation (TES), motor evoked potential (MEP), somatosensory evoked potential (SSE), phase reversal of somatosensory evoked potential, evoked potential, electrocorticography (ECoG), direct cortical electrical stimulation (DCES), microelectrode recording (MER) or local field potential recording (LFP).

In some embodiments, the device is coupled to software that enables the real time or retrospective review of data coming from different navigation, monitoring and diagnostic tools used during the diagnostic procedure. For example, in various embodiments, the monitoring device can take many different forms. In some implementations, the monitoring device is a dedicated electrical circuit employing various sensors, logic elements, and actuators. In other implementations, the monitoring device is a computer-based system that includes a programmable element, such as a microcontroller or microprocessor, which can execute program instructions stored in a corresponding memory or memories. Such a computer-based system can take many forms, may include many input and output devices, and may be integrated with other system functions, such as the monitoring device, imaging device, a computer network, and other devices that are typically employed during a procedure. For example, a single computer-based system may include a processor that executes instructions to provide the function of the monitoring device; display imaging information associated with a procedure (e.g., from an imaging device); display pressure, temperature, time information and tip position; and serve as an overall interface for the device. In general, various types of monitoring devices are possible and contemplated, and any suitable monitoring device can be employed.

In certain embodiments, the device may include switches for manually controlling the operation of the device by a medical practitioner. The switches can provide functions such as on/off, administering electrical current, and predetermined cycles of administering current by selectively and controllably communicating with the electrical generator.

In some embodiments, the device can be operatively connected to semi-steerable or navigational sources for easier guidance into the intervertebral disc. In various embodiments, the navigational sources can be coupled with a pre-procedure such as, for example, CT, MRI, PET scan, etc. so that the target intervertebral disc can be identified and accurately located during diagnostics and treatment.

In various embodiments, the device may include radiographic markers to help indicate position on imaging procedures (e.g., CT scan, X-ray, fluoroscopy, PET scan, etc.). These may be disposed on or a portion of the device and include, but are not limited to, barium, calcium phosphate, and/or metal beads.

In some embodiments, the device can also be utilized to detect and treat pain from other spinal abnormalities, such as, compression fractures, pars defects, vertebral instability, soft tissue abnormalities in ligaments, tendons, muscles, cartilaginous structures, joints (e.g., facet joints, sacroiliac joints, etc.) or abnormalities resulting from tumors, infection or other infiltrative processes. Pain resulting from nerve root lesions (e.g., compressive lesions from adjacent discs, hypertrophic facet joints, facet joints cysts, faulty hardware positioning, bony foraminal encroachment, spondylolisthesis, spondylolysis, congenitally short pedicles, nerve sheath tumors, granulation tissue and/or arachnoiditis, etc.), spinal nerve compression (e.g., spinal stenosis), peripheral nerve lesions, femoral neuropathy, meralgia paresthetica, peroneal neuropathy, asymmetrical neuropathies, lower limb joint pathology, vascular pathology, degenerative disc and joint disease or the like.

Figure 7:
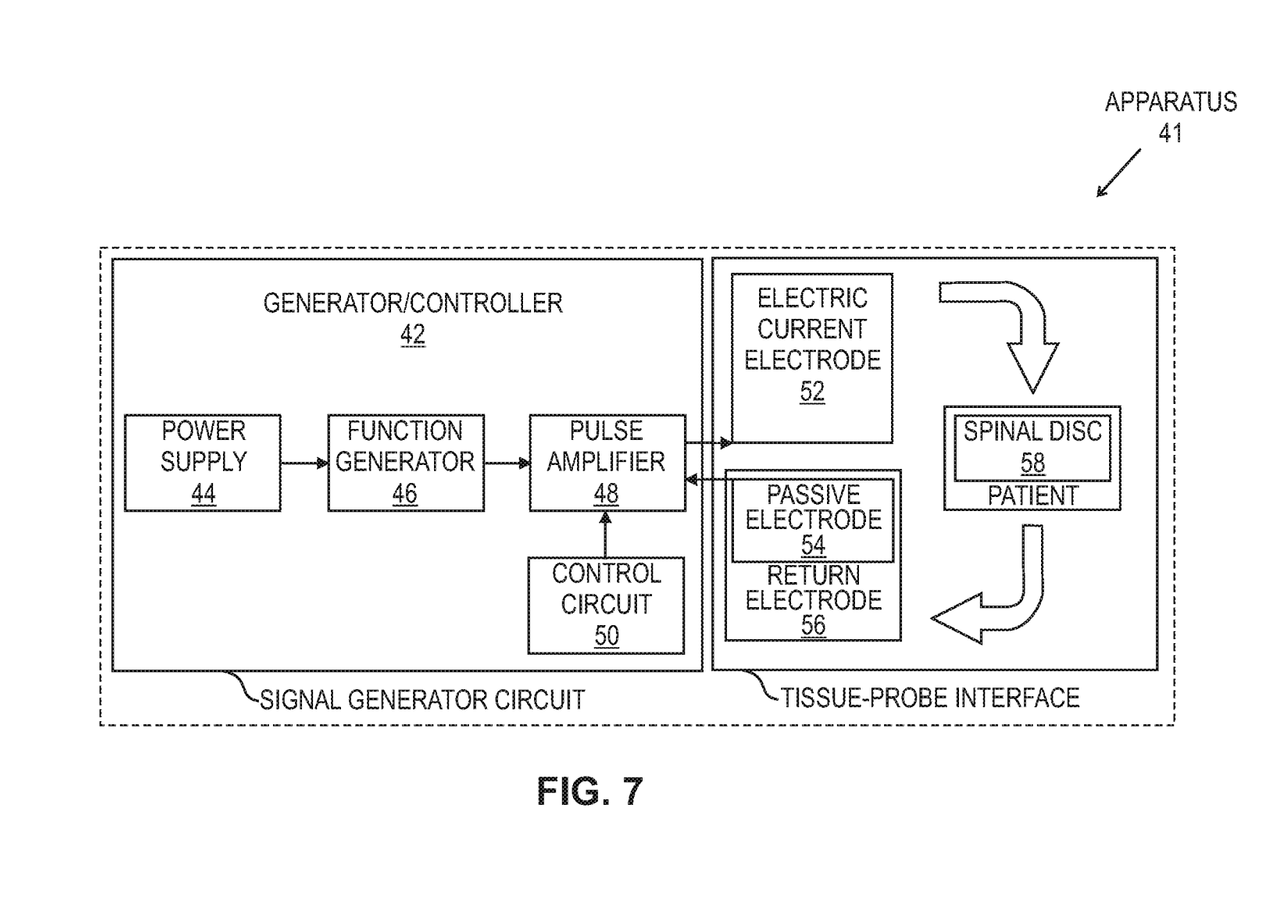
FIG. 7 is a schematic diagram illustrating an embodiment of the apparatus for administering electrical current to the intervertebral disc in accordance with teachings disclosed herein.

FIG. 7 illustrates a schematic flow diagram of an apparatus 41 for providing electrical current treatment in accordance with some embodiments disclosed herein. FIG. 7 shows the interface between a generator/controller and a cannula having an electrical current electrode 52 for providing current to the spinal disc 58, and a return electrode 56 and a passive electrode 54. The generator/controller 42 comprises a control circuit 50, a power supply 44, a function generator 46, and an electrical pulse amplifier 48. The signal generator circuit allows for electrical current to be generated and operated under the generator/controller 42, which allows a specific setting for electrical current generation and control of the current as well as the desired pulse, on/off or pause control of the electrical energy. The apparatus with the sensor (not shown) can also measure tissue impedance as the device contacts the intervertebral disc to monitor a pain response at the tissue electrode interface.

It will be understood that although electrical current electrode 52, the passive electrode 54 and return electrode 56 are shown as separate electrodes, they can be in one cannula or they can be in separate cannulas. It will also be understood that the passive electrode or return electrode, in some embodiments, can receive and conduct electrical current away from the target tissue site (e.g., intervertebral disc), which can then be used by the control circuit to monitor the electrical current delivered to the tissue.

The return electrode, passive electrode and/or electrical current electrode may be of any designs, sizes or shapes. The return electrode, passive electrode and/or electrical current electrode can be integral with the cannula or separated from it.

In some embodiments, the return electrode 56 can receive, conduct and discharge electrical energy at the electrical current electrode 52. In some embodiments, this is accomplished by a switch member that splits the electrical energy or directs the electrical energy to the return electrode.

Figure 8:
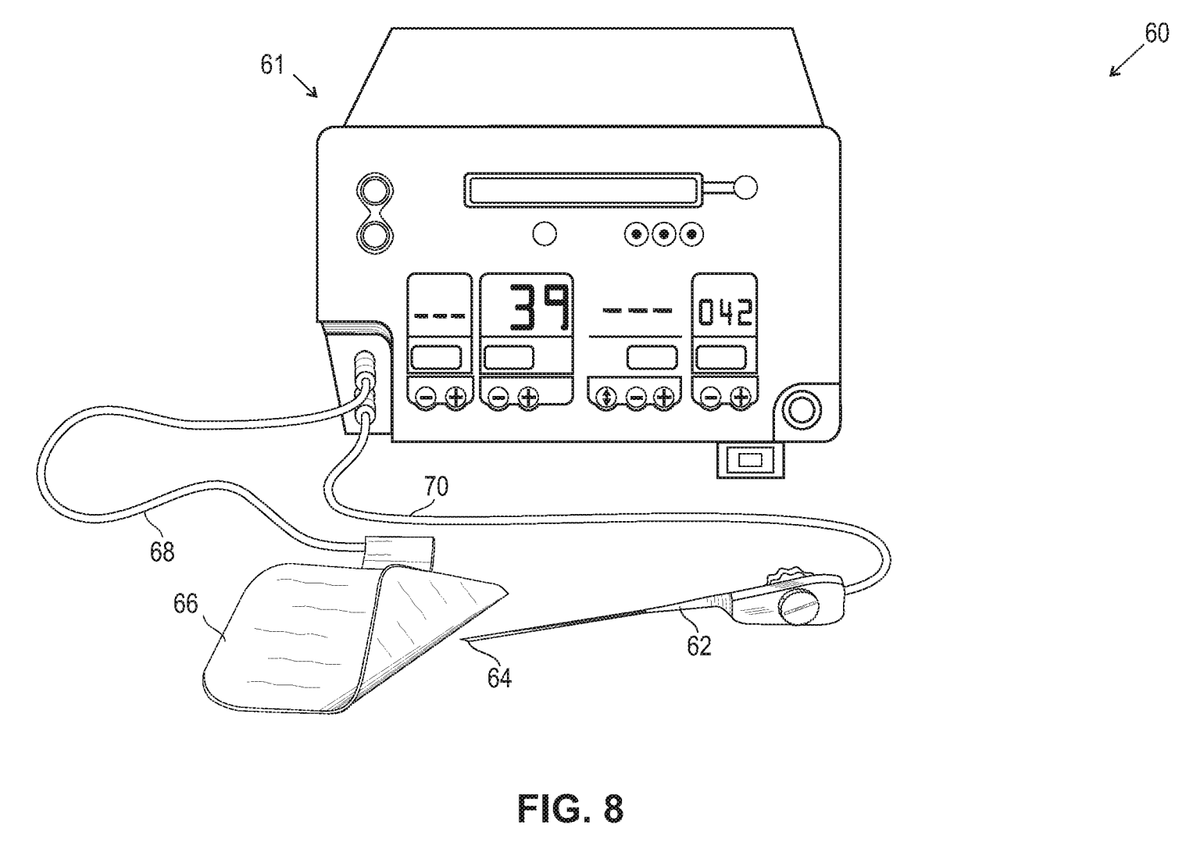
FIG. 8 shows an electrical current administering device and computer control system for the electrical current apparatus.

In some embodiments, an apparatus for providing electrical current treatment comprises a device for providing electrical current treatment and an electrical connection assembly configured to electrically couple the electric current electrode to a power supply 44 that is part of a generator/controller 42 that can convert the energy to the appropriate electrical current, of which further details, in some embodiments, are described in FIG. 8.

FIG. 8 shows another embodiment of an apparatus 60 for providing electrical current treatment, illustrating the physical units described schematically in FIG. 7. Shown in FIG. 8 are, in accordance with some embodiments, an electrical current electrode 62, a generator/controller 61, and a return electrode 66. Electrical energy is conducted to the electrical current electrode 62 and electric current is discharged from the beveled tip 64 via connector 70 and electrical energy is returned to the return electrode 66 via connector 68. The electrical energy can return after contacting the target tissue site (e.g., the intervertebral disc) and the pain response monitored. In some embodiments, the return electrode can comprise a recording electrode to record electric potentials.

Methods

The present disclosure also provides methods for diagnosing and/or treating discogenic back pain. Examples of discogenic back pain include, but are not limited to bulging, herniated, and/or ruptured discs.

In some embodiments, a method of diagnosing discogenic back pain is provided. The method comprises administering electrical current from a device to a region of the intervertebral disc, the device comprising a cannula having a proximal end and a distal end and a longitudinal axis therebetween, the distal end comprising a beveled tip for contacting a region of the intervertebral disc, an electrode disposed within or on a surface of the cannula adjacent to the distal end, the electrode configured to discharge electrical current to the region of the intervertebral disc. It is to be understood that the device is device 10, as disclosed herein.

In some embodiments, the method further comprises identifying the discogenic back pain by detecting a positive pain response from the patient when the electrical current is administered. In some embodiments, the method further comprises injecting the selected area of the disc identified with the positive pain response with a local anesthetic and a neurotoxin administered by the needle to treat the selected area of the disc with the positive pain response.

In some embodiments, the proximal end of the device is configured to be coupled to an electrical generator comprising an electrical pulse generator. In some embodiments, the region of the intervertebral disc comprises an annulus fibrosus of the intervertebral disc.

In some embodiments, a method of diagnosing and treating discogenic back pain is provided. The method comprises administering electrical current from a device to a region of the intervertebral disc, the device comprising a cannula having a proximal end and a distal end and a longitudinal axis therebetween, the distal end comprising a beveled tip for contacting a region of the intervertebral disc, an electrode disposed within or on a surface of the cannula adjacent to the distal end, the electrode configured to discharge electrical current to the region of the intervertebral disc to evoke a pain response; and administering an effective amount of a neurotoxin to the intervertebral region to reduce the back pain. It is to be understood that the device is device 10, as disclosed herein.

In some embodiments, the method further comprises positioning a patient such that the patient flexes the spine before the administering electrical current step. In some embodiments, the electrical current is administered to a region of the intervertebral disc comprising a selected area of a healthy first disc of a patient, and the method further comprises recording a first evoked action potential threshold of the first disc of the patient.

In some embodiments, the method further comprises administering electrical current to a selected area of a second disc of the patient with the device; identifying the discogenic back pain by detecting a positive pain response from the patient when the electrical current is administered to the selected area of the second disc; recording a second evoked action potential threshold of the second disc of the patient; and comparing the first evoked action potential threshold with the second evoked action potential threshold to treat the back pain.

In several embodiments, the methods disclosed herein include operatively coupling the device to a source of navigational capability to allow easier insertion and/or pushing through the tissues. In various embodiments, the methods disclosed herein can include a pre-procedure step wherein the deice can be coupled to a CT or MRI machine so that the disc can be identified and accurately located.

Kit in various embodiments, a kit is provided comprising the device. The kit may include additional parts along with the device combined together to be used to diagnose and/or treat discogenic back pain. The kit may include the device in a first compartment. The second compartment may include a vial and/or a syringe for storing a local anesthetic, an anti-inflammatory, a neurotoxin, and/or any instruments needed for the procedure. A third compartment may include gloves, drapes, wound dressings and other procedural supplies for maintaining sterility of the diagnostic and/or treatment site, as well as an instruction booklet, which may include a chart that shows how to implement the device. A fourth compartment may include additional needles and/or sutures. Each tool may be separately packaged in a plastic pouch that is sterilized. A fifth compartment may include an agent for radiographic imaging. A cover of the kit may include illustrations of the diagnostic and/or treatment procedures and a clear plastic cover may be placed over the compartments to maintain sterility.

These and other aspects of the present application will be further appreciated upon consideration of the following Examples, which are intended to illustrate certain particular embodiments of the application but are not intended to limit its scope, as defined by the claims.

EXAMPLES

Example One

Figure 1:
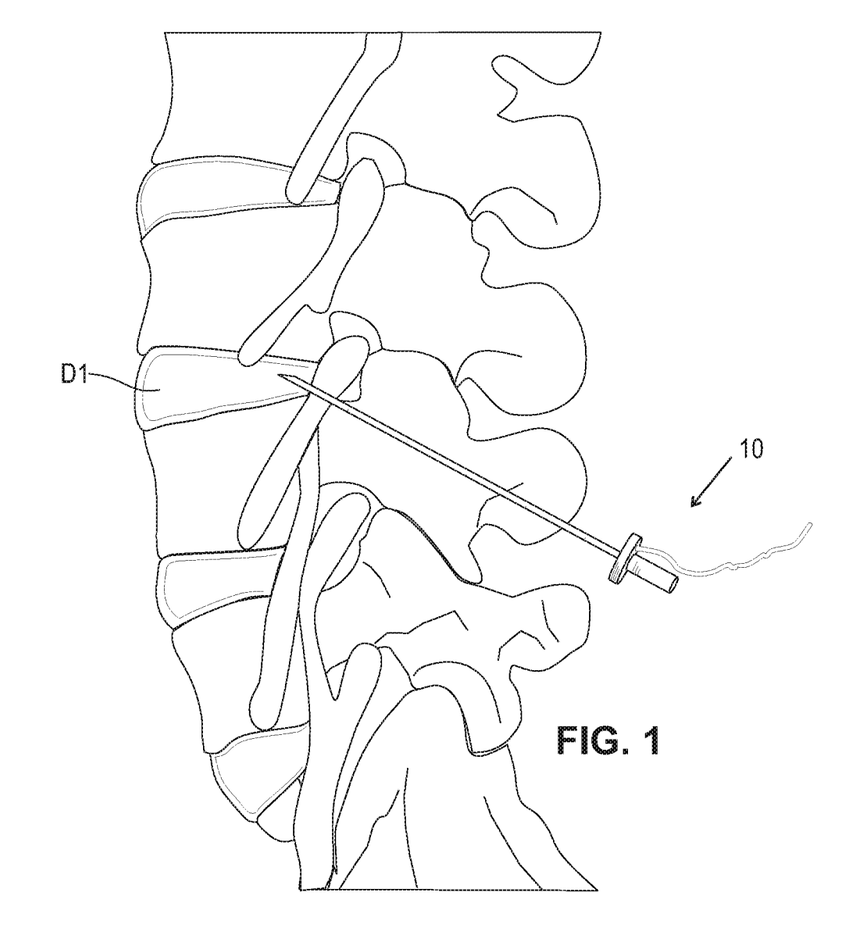

As shown in FIG. 1, the cannula of the device (e.g., device 10 described herein) will be directed toward the dorsolateral annulus fibrosus of an intervertebral disc D1 under image guidance. For the diagnostics phase, the needle will not be advanced past the outermost layers of the annulus fibrosus. The beveled tip of the cannula with an integrated electrode facilitates separation of the collagenous fibers of the annulus fibrosus when the device is rotated parallel to the lamella of the annulus fibrosus. Constant current pulses in the range of 2 to about 20 mAMP will be delivered to the outer annulus fibrosus. Concordant pain, and especially that evoked at the lower end of the current range, is consistent with nerve ending sensitization and discogenic pain (e.g., positive diagnosis). A syringe can then engage the port of the device for administration of a local anesthetic. The device can then be advanced for delivery of therapeutic agents such as an anti-inflammatory and/or a neurotoxin, and then repositioned consistent with maximal sensitivity during the diagnostic phase.

Example Two

Figure 5A:
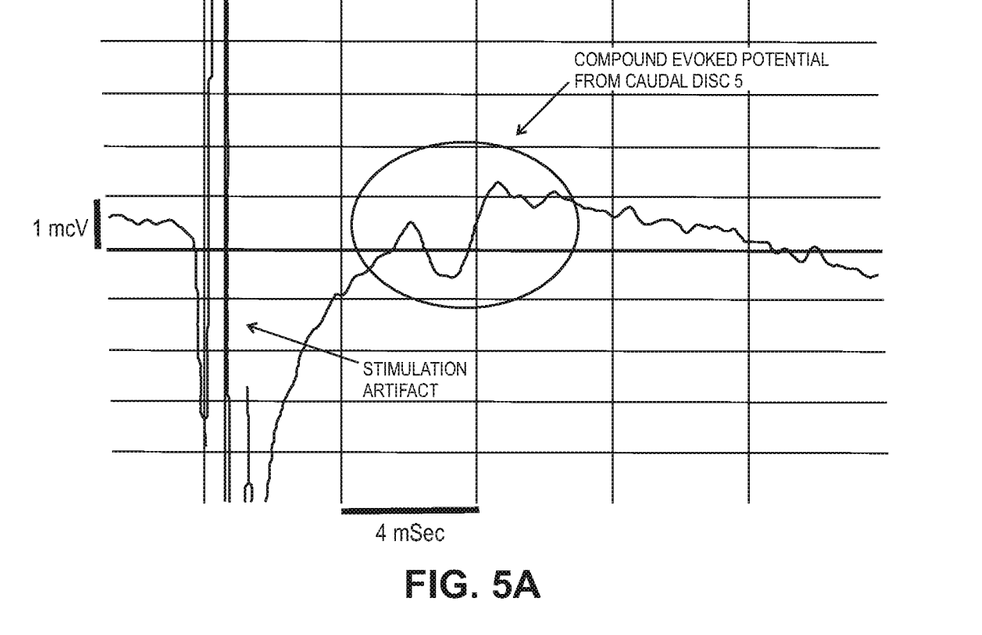
FIG. 5A depicts a graph of results of compound action potentials evoked from caudal disc 5 (tail) in the lumbar spinal cord of Sprague Dawley rats. Following a 10 mAMP pulse of current into the naïve tail disc, a compound evoked potential arrived in the spinal cord with an initial peak corresponding to about 8 meters/second and a secondary peak corresponding to about 5 meters/second NCV.
Figure 5B:
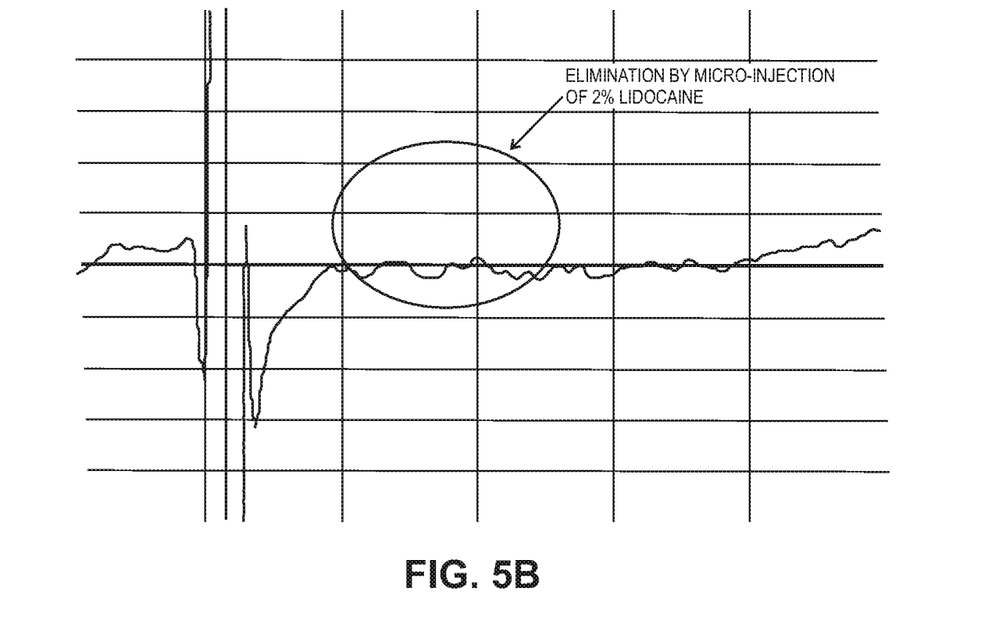
FIG. 5B depicts a graph of results of injecting lidocaine into the caudal disc 5 in the lumbar spinal cord of the Sprague Dawley rats after the 10 mAMP pulse of current was administered to the rat (FIG. 5A). Intradiscal injection of 2% lidocaine (10 µL) completely eliminated evoked potentials for at least 30 minutes.

Sprague Dawley rats were tested for compound action potentials evoked from caudal disc 5 (tail) in the lumbar spinal cord when a current was emitted from device 10 to the site. Following a 10 mAMP pulse of current emitted from the device into the naïve tail disc, a compound evoked potential arrived in the spinal cord with an initial peak corresponding to about 8 meters/second and a secondary peak corresponding to about 5 meters/second nerve conduction velocity (NCV), as shown in FIG. 5A. An intradiscal injection of 2% lidocaine (10 µl) completely eliminated evoked potentials for at least 30 minutes, as shown in FIG. 5B.

Example Three

A test was performed to evaluate whether positional changes, such as, flexing of the spine during diagnostics for determining discogenic pain would be beneficial. For example, it was postulated that flexing the spine during diagnostics could potentially magnify the difference between a healthy disc and a symptomatic disc with respect to evoked potential threshold when the patient is situated in a non-neutral position.

Figure 6A:
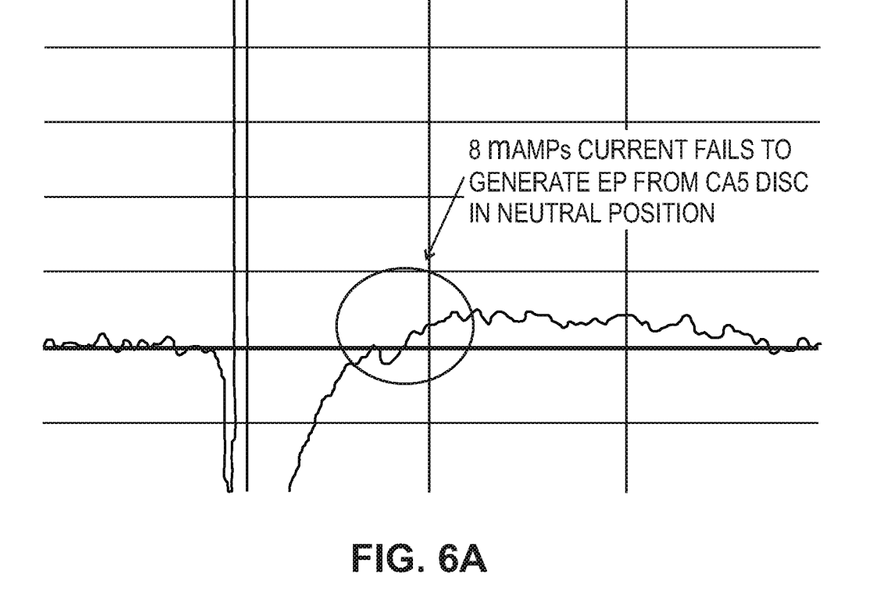
FIG. 6A is a graph depicting results that show that flexing a disc into positional changes may lower the evoked potential threshold. Following administration of an 8 mAMP pulse of current into a tail disc of a Sprague Dawley rat disposed in a neutral position, a compound evoked was not detected in the lumbar spinal cord.
Figure 6B:
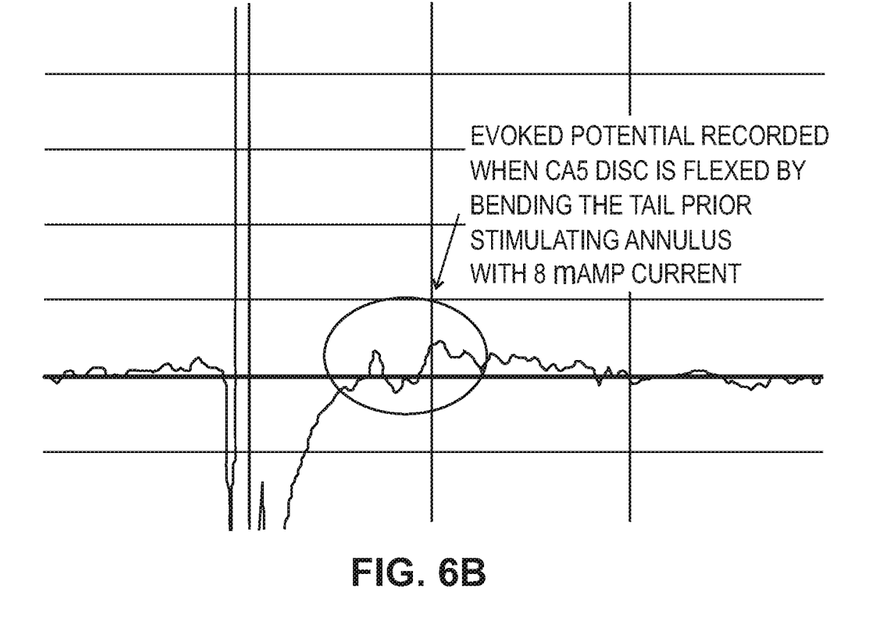
FIG. 6B is a graph showing that when the tail of a Sprague Dawley rat was bent to place mixed compressive/tensile strain on caudal disc 5, the 8 mAMP pulse did generate a mixed potential distinguishable from noise. It was hypothesized that the difference between a healthy and symptomatic disc in the threshold current required to elicit concordant pain or an evoked potential may be amplified by spinal flexion or extension.

As shown in FIG. 6A, Sprague Dawley rats were administered an 8 mAMP pulse of current into a tail disc in a neutral position. A compound evoked was not detected in the lumbar spinal cord. However, as shown in FIG. 6B, when the tail of the rat was then bent to apply mixed compressive/tensile strain on caudal disc 5, an 8 mAMP pulse did generate a mixed potential distinguishable from noise. Results indicated that the difference between a healthy disc and a symptomatic disc in the threshold current required to elicit concordant pain or an evoked potential may be amplified by spinal flexion or extension.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A device for providing electrical current to an intervertebral disc, the device comprising a cannula having a proximal end and a distal end and a longitudinal axis therebetween, the distal end comprising a beveled tip for contacting a region of the intervertebral disc; an electrode disposed within or on a surface of the cannula adjacent to the distal end, the electrode configured to discharge the electrical current to the region of the intervertebral disc, wherein the beveled tip has an air gap disposed in an inner layer of the beveled tip and the electrode is adjacent to the beveled tip such that the air gap insulates the electrical current and the electrical current is discharged only through the beveled tip, wherein the region of the intervertebral disc comprises an annulus fibrosus of the intervertebral disc such that the beveled tip is configured to facilitate separation of collagenous fibers of the annulus fibrosus by rotating parallel to a lamella of the annulus fibrosus.

2. The device of claim 1, wherein the proximal end is configured to be coupled to an electrical generator.

3. The device of claim 2, wherein the electrical generator configured to be coupled to the proximal end is an electrical pulse generator.

4. The device of claim 1, wherein the electrode is configured to discharge from about 0.5 to about 50 mAMP pulses of current.

5. The device of claim 4, wherein the electrode is configured to discharge from about 2 to about 20 mAMP pulses of current.

6. The device of claim 1, wherein the cannula comprises an insulation material in addition to the air gap.

7. The device of claim 1, wherein the cannula comprises a port for engagement with a syringe.

8. The device of claim 7, wherein the syringe configured for engagement with the port is configured for administration of a local anesthetic, an anti-inflammatory and/or a neurotoxin.

9. The device of claim 8, wherein the neurotoxin is configured to be administered in an amount of 1 to about 100 µM to a selected area of the intervertebral disc.

10. The device of claim 9, wherein the neurotoxin configured to be administered comprises inhibitors of sodium channels, neurotoxins targeting transient receptor potential cation channel subfamily V member 1 (TRPV1), botulinum toxins or a combination thereof.

* * * * *